United States Patent
Van de Velde

(10) Patent No.: US 7,374,287 B2
(45) Date of Patent: May 20, 2008

(54) RELAXED CONFOCAL CATADIOPTRIC SCANNING LASER OPHTHALMOSCOPE

(75) Inventor: Frans J. Van de Velde, Boston, MA (US)

(73) Assignee: Jozef F. Van De Velde, Oosterzele (BE)

( * ) Notice: Subject to any disclaimer, the term of this patent is extended or adjusted under 35 U.S.C. 154(b) by 426 days.

(21) Appl. No.: 11/182,538

(22) Filed: Jul. 15, 2005

(65) Prior Publication Data
US 2006/0176448 A1     Aug. 10, 2006

(51) Int. Cl.
*A61B 3/10* (2006.01)

(52) U.S. Cl. ..................................... 351/221

(58) Field of Classification Search ............... 351/205, 351/206, 221, 246, 200, 208–211; 434/258; 359/497; 606/4, 5
See application file for complete search history.

(56) References Cited

U.S. PATENT DOCUMENTS

| | | | | |
|---|---|---|---|---|
| 4,764,005 A | * | 8/1988 | Webb et al. | 351/205 |
| 5,374,193 A | * | 12/1994 | Trachtman | 434/258 |
| 5,903,388 A | * | 5/1999 | Sedlmayr | 359/497 |

* cited by examiner

*Primary Examiner*—George Manuel

(57) ABSTRACT

A number of additional embodiments and optical constructions of a relaxed confocal catadioptric scanning laser opthalmoscope (SLO) are disclosed. They improve the functionality of microperimetry (MP), and the integration of the existing instrument with the capabilities of high speed spectral domain optical coherence tomography (SD-OCT). The improvements pertain to enhanced acousto-optic modulation with regard to rise-time and combination of wavelengths, enhanced control of illuminating beam characteristics and separation of illuminating and returned light within the SLO, enhanced electronic control and options for the galvanometer—polygon combination, additional use of a liquid crystal spatial light modulation, and the modalities under which SD-OCT can be integrated within the SLO.

6 Claims, 6 Drawing Sheets

Prior Art $$\theta_B = \sin\theta_B = \lambda/2\Lambda$$

$$\Lambda = v_{sound} / f_{modulator}$$

$$\theta_B = \lambda/2 \times f_{modulator} / v_{sound}$$

RELAXED CONFOCAL CATADIOPTRIC SCANNING LASER OPHTHALMOSCOPE

CROSS REFERENCE TO RELATED APPLICATIONS

This application is related to U.S. Pat. Nos. 6,186,628 and 6,789,900. These patents are incorporated in this application by reference.

BACKGROUND

1. Field of Invention

The invention relates generally to instruments for examining and treating the eye and specifically to a scanning laser opthalmoscope (SLO) based on a relaxed confocal catadioptric design, in combination with various external light sources, and optimized for advanced non-invasive diagnostic procedures, optical coherence tomography (OCT) and microperimetry (MP).

2. Description of Prior Art

The opthalmoscope is well known as an important device for examining the eye, and in particular the retina. As a result of great interest in preserving eyesight, opthalmoscopes of various constructions have been built. The latest version of the opthalmoscope, a scanning laser opthalmoscope, is particularly appealing because of its unique capability of combining a high resolution and high contrast infra-red or angiographic 60 Hz interlaced video imaging of the retina with psychophysical procedures such as microperimetry. A precise correlation between retinal anatomy and retinal functioning can be established with the scanning laser opthalmoscope. This retinal function mapping that includes information about fixation characteristics, visual acuity and retinal sensitivity, is now known to be very helpful to the surgeon when applying various forms of therapeutic laser and for the purpose of low vision rehabilitation. Van de Velde has disclosed before in U.S. Pat. Nos. 5,892,569, 5,923,399, 5,943,117, 6,186,628 and 6,789,900, which are all herein incorporated by reference, different embodiments of the relaxed confocal scanning laser opthalmoscope that use various external light sources for therapeutic and diagnostic applications. Such functional extensions of the basic instrument rely to a great extent on its relaxed confocal and catadioptric design, incorporating one or two synchronized avalanche photodetector pathways.

Additional extended functionality has been disclosed in the U.S. Pat. Nos. 5,543,866, 5,568,208 and 6,000,799, herein incorporated by reference. Such embodiments have been constructed and the results have been reported in the following publications, that are herein incorporated by reference:

1. Frans J. Van de Velde. Quantitative SLO microperimetry for clinical research in age related maculopathy. In: Non-invasive assessment of the visual system: from the Topical Meeting Vision Science and its Applications, Jan. 31-Feb. 3, 1997, Santa Fe, N. Mex./edited by Dean Yager; sponsored by Optical Society of America; in cooperation with the American Academy of Optometry. Published/Created: Washington, D.C.: The Society, 1997: 42-47. ISBN: 1557524718 (Library of Congress).
2. Frans J. Van de Velde. Role of the scanning laser opthalmoscope in photodynamic therapy of macular disease Publication: Proc. SPIE Vol. 3908, p. 190-201, Ophthalmic Technologies X; Pascal O. Rol, Karen M. Joos, Fabrice Manns; Eds. Publication date: June 2000.
3. Frans J. Van de Velde. Scanning laser opthalmoscope optimized for retinal microphotocoagulation. Publication: Proc. SPIE Vol. 3564, p. 146-157, Medical Applications of Lasers in Dermatology, Cardiology, Opthalmology, and Dentistry II; Gregory B. Altshuler, Stefan Andersson-Engels, Reginald Birngruber, Peter Bjerring, Adolf F. Fercher, Herbert J. Geschwind, Raimund Hibst, Herbert Hoenigsmann, Frederic Laffitte, Henricus J. Sterenborg; Eds. Publication date: February 1999.
4. Frans J. Van de Velde et Al. Scanning laser retinoscopy: a new technique for evaluating optical properties of the cornea after refractive surgery Publication: Proc. SPIE Vol. 3192, p. 187-194, Medical Applications of Lasers in Dermatology, Opthalmology, Dentistry, and Endoscopy; Gregory B. Altshuler, Reginald Birngruber, Marco Dal Fante, Raimund Hibst, Herbert Hoenigmann, Neville Krasner, Frederic Laffitte; Eds. Publication date: December 1997.
5. Frans J. Van de Velde. Scanning laser opthalmoscopy: optimized testing strategies for psychophysics Publication: Proc. SPIE Vol. 2930, p. 79-90, Lasers in Opthalmology IV; Reginald Birngruber, Adolf F. Fercher, Philippe Sourdille; Eds. Publication date: December 1996.

OBJECT, SUMMARY AND ADVANTAGES OF THE INVENTION

It is the principle object of this invention to disclose additional embodiments and optical constructions of the aforementioned relaxed confocal instrument (SLO) that further improve the functionality of microperimetry (MP), and especially integrate the existing instrument with the capabilities of spectral domain optical coherence tomography (SD-OCT).

In summary, the improvements to the generic relaxed confocal catadioptric instrument, combined with external light sources for MP and OCT include:

1) Improved acousto-optic modulation (AOM) of the scanning lasers relating to a sufficiently short rise-time parameter and the combination of laser wavelengths, resulting in a more efficient modulation design with better microperimetry, region and timing-of-interest angiography, enhanced suppression of unwanted light reflexes, and specifically an integration of high-speed spectral domain OCT.
2) An enhanced control of the separation of the illuminating and detecting light pathways within the SLO permitting control of the profile and diameter of the scanning beams, with or without beam truncation, and enabling the photodetection of on-axis returned light, useful in many diagnostic applications that use external light sources.
3) Different scanning characteristics of the galvanometer—polygon combination, permitting the use of a zoom, and specifically a high intensity background, higher resolution potential acuity measurement microperimetry, even with a limited RPM value of the polygon and limited galvanometer capability.
4) Alternative Maxwellian view external projection methods, including the use of a liquid crystal spatial light modulator (LC-SLM) within a Maxwellian view projection channel for the use of microperimetry, analogous to a previously described method for selective PDT or TTT treatment.
5) The modalities under which a combination of the relaxed confocal SLO and SD-OCT becomes feasible, especially with regard to wavelength interferences, eye-movements and representation of results at video-rates in near real-time.

Further objects and advantages of the proposed embodiments will become apparent from a consideration of the drawings and ensuing description of a preferred embodiment.

REFERENCE NUMERALS IN DRAWINGS

Figure 1:
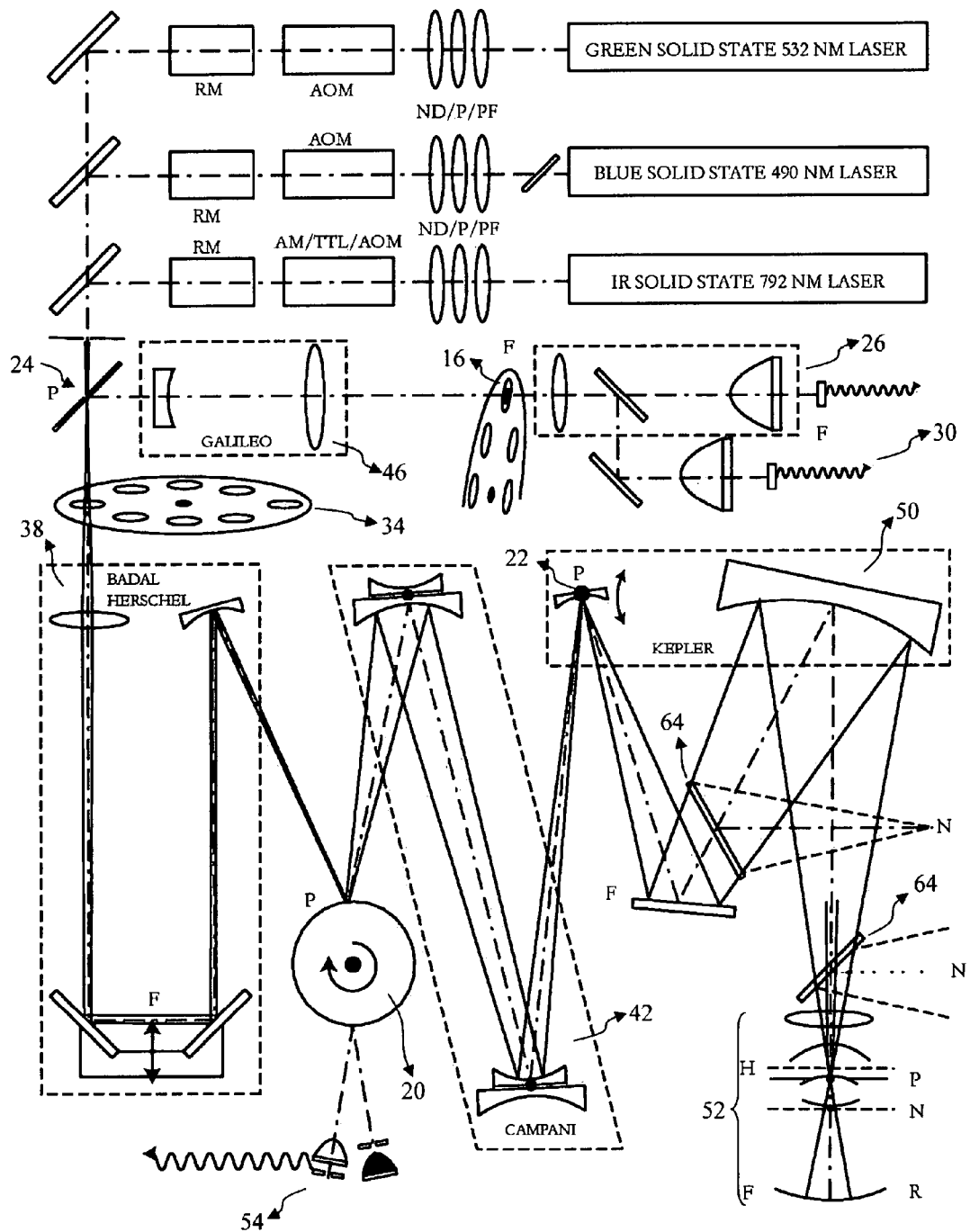
FIG. 1 is a diagrammatic representation of prior art, illustrating the illuminating pathway of a relaxed confocal scanning laser opthalmoscope, including the two options for attaching external scanning or non-scanning laser sources. To be noted is the modular composition of the SLO optics. Some modules could be omitted in an otherwise fully functional SLO.
Figure 2:
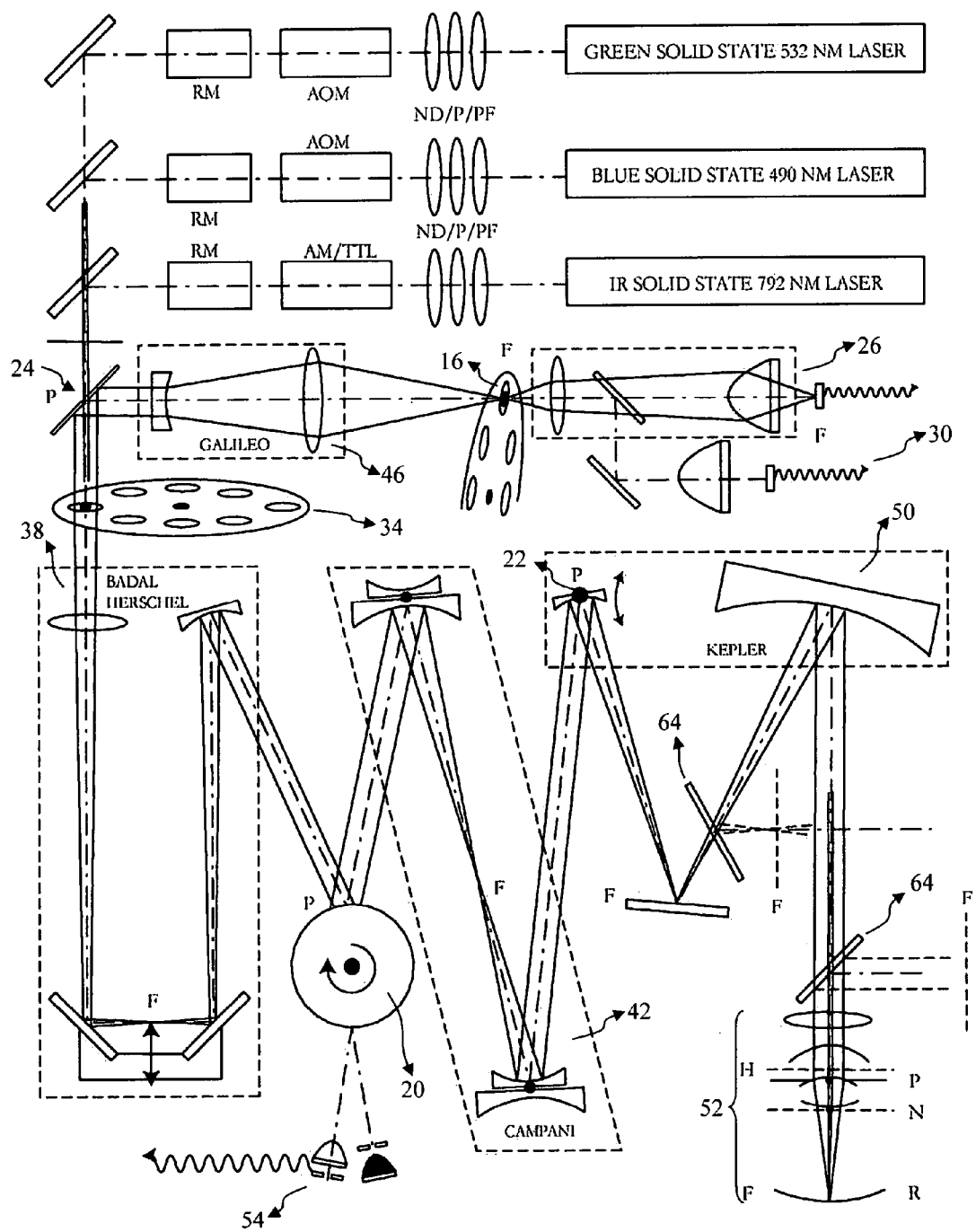
FIG. 2 details a prior art SLO with the return path of the scanning laser light after having been scattered by the retinal tissue and reflected from the cornea.

10 Infrared and visible wavelength solid state laser sources
12 Neutral density (ND), Polarizing (P) and Pre-focus (PF) beam conditioning, Radiometer (RM)
14 Amplitude (analog) modulation (AM), TTL digital modulation, AOM modulation (low bandwidth)
16 Confocal aperture in the object plane
18 Confocal aperture in the image plane
20 Second scanning element, polygon with number of mirror facets and turning at specified RPM
22 First scanning element, galvanometer mirror steered by ramp signal
24 Central and separating aperture
26 Avalanche Photodiode (APD) detection optical pathway
30 Optional secondary synchronized APD optical detection pathway
34 Prefocusing lens wheel
38 Badal-Herschel ametropia correction module
42 Campini like invertible telescopic optical zoom module
46 Optional Galilean beam expander module
50 Main mirror laser raster projection module
52 Schematic eye optics with cardinal planes F, N, H, lens, cornea and anatomical pupil
54 Master synch signal generator with slit shaped light source, double detector arrangement
58 Start of Scan (SOS) TTL generator
62 Servo PLL based feedback control of RPM speed of polygon
64 Beam splitter coupling with the SLO (two optical possibilities)
66 High bandwidth acousto-optic modulator (AOM)
70 Wavelength lambda dependent Bragg angle theta
74 First order diffracted (modulated) beam
78 Prism, wedge prism
82 Collimated Gaussian laser beam (1 mm)
86 Reduced beam diameter (0.2 mm)
90 Shorter wavelength
94 Longer wavelength
98 Collimator, Galilean collimator
102 Off-axis entrance of first element of collimator
104 Angulated second element of collimator
112 Central aperture with coating to return light from the retina to the detector
116 Central aperture for a variable size and shape truncation
120 Rotating wheel with several separating apertures
124 Larger diameter collimated Gaussian beam, for example 2 mm
128 Smaller diameter collimated Gaussian beam, for example 1 mm
132 Truncated beam, for example 1 mm, with a flatter beam profile
136 Detailed histological retina and choroid sectioning
138 Retina and choroid sectioning (schematic)
140 A smaller focused spot size with smaller depth of focus (Gaussian beam formulation)
144 A larger focused spot size with larger depth of focus (Gaussian beam formulation)
148 A smaller diffraction limited spot size with larger depth of focus
152 A pair of anamorphic prisms
156 Single mode monochromatic light source
160 Focusing lenslet
164 Coherence breaking (mode scrambling) diffuser
168 Pinhole, for example 50 micron in diameter
172 Optional diverging lens
176 N.A. limiting aperture
180 Collimator lens
184 Spatial Light Modulator under CPU control in retinal conjugate plane
188 Focusing lens (and additional lens groups for ametropia correction)
196 Anatomical pupil of the eye with Maxwellian view projection
200 Schematic 60 D eye optics
208 Superluminescent diode or other broadband light source
212 Grating
216 Linear detector array
220 "Fourier machine" generating OCT data
224 Reference mirror, Michelson interferometer set-up 228 x-y projection mechanism (spherical, pivoting like)
236 x-y retinal scanning (relaxed confocal SLO)
240 z retinal scanning (SD-OCT)
242 Beam steering control
244 Spatial—temporal electronic multiplexer DETAILED DESCRIPTION AND OPERATION
OF THE IMPROVEMENTS TO THE RELAXED
CONFOCAL SCANNING LASER
OPHTHALMOSCOPE A typical embodiment of the relaxed confocal scanning laser opthalmoscope adaptable for several functional extensions is illustrated in the FIGS. 1 and 2. The principles of scanning laser opthalmoscopy are described in detail in the prior art (Pomerantzeff, Webb, Hughes, Saban-Cohen et Al., Plesch and Klingbeil, Van de Velde). Only the features of the relaxed confocal scanning laser opthalmoscope that are relevant to the enhancements are further discussed.

I. Enhanced Acousto-Optic Modulation

The use of an acousto-optic modulator to draw a variety of objects in the visible laser raster dates back to the proposals of Hughes and Webb. Before that, a slide or screen was used at a confocal retinal plane to generate psychophysical stimuli. In its simplest embodiment, a typical collimated Gaussian laser beam of about 1 mm diameter traverses the AOM at the well-known Bragg angle. The first order diffracted beam is used with about 85% efficiency. Modulation can occur over a dynamic range of several magnitudes of intensity. It was quickly noted that if a two laser system was used for separate imaging and psychophysics purposes, the acousto-optical delay time would have to be taken into account, software or hardware wise. Typically this delay is about 50 pixels of each 90 ns duration, i.e. about 0.5 microseconds. Fortunately, this delay is a stable value.

It was also suggested at that time, but never reduced to practice, that a prism could be directly attached to both ends of this AOM in order to combine two or even more wavelengths, presumably at their optimal Bragg angle.

Figures 3, 4:
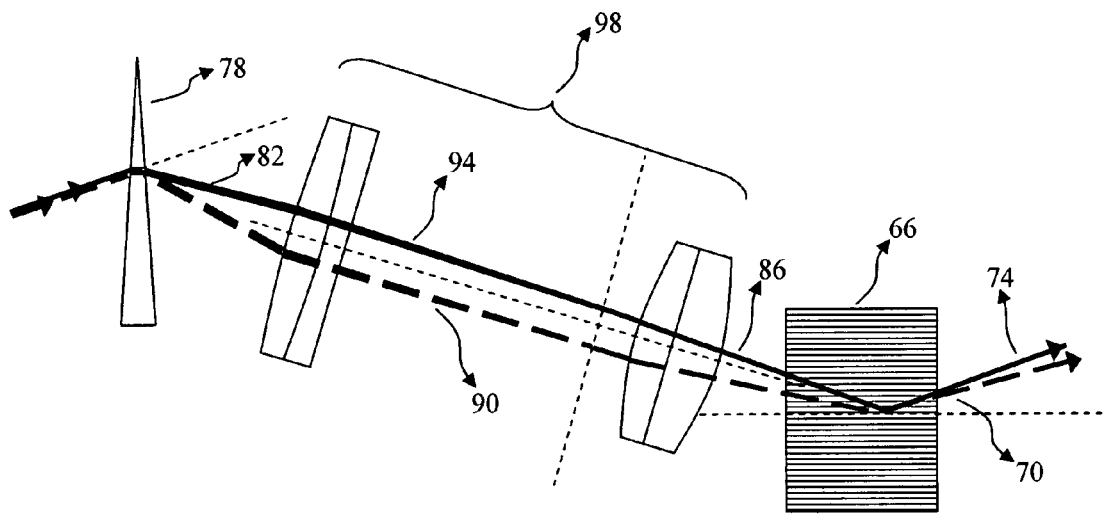
FIGS. 3 a and b detail the improved AOM modulation configuration including beam diameter reduction and combination of wavelengths.
FIG. 4 incorporates formulas relating wavelength $\lambda$, Bragg angle $\theta_B$ and AOM parameters $\Lambda$, $v_s$, $f_{mod}$ FIGS. 5 a and b show the penetration of Gaussian beams into the retina and the relative positioning and size of the confocal aperture for two different external beam diameters (ebd) of 1 and 2 mm; focused beam waist (fbw); relaxed confocal aperture (rca); Raleigh zone (rz).

Two problems have been observed with regard to the above. First, detailed psychophysics requires a much higher bandwidth of modulation in order to correctly and evenly represent the correct light intensity of single pixel objects. This is particularly clear in the case of the smallest acuity targets (about 1.5 minarc on the retina) that are possible within the laser raster. The second problems relates to the prism. From the Bragg formula (FIG. 4) it can be seen that shorter wavelengths require a smaller Bragg angle and vice-versa upon entering the AOM. A prism however will cause the shorter wavelength 90 to have a larger Bragg angle 70 and could therefore not be used as previously illustrated in the prior art. Both problems can be solved at the same time with an appropriate optical construction.

In order to decrease the rise-time for modulating the traversing laser beam, it is necessary to focus and collimate the original 1 mm beam 82 to a size that is approximately 0.2 mm 86. In order to accomplish this, the AOM 66 has to be driven at a higher frequency, 80 MHz at a minimum. To reduce this beam diameter a Galilean collimator 98 can be used. If this collimating telescopic lens system is used after the prism 78, then the divergence of wavelengths 90, 94 is switched and corresponds to the correct configuration to enter the AOM 66.

Actual prism values to be used and lens distances to be observed depend on the refractive index of the prism glass, desired Bragg angles and power of the telescope, but are readily calculated from tables provided by Melles-Griot, Inc. Also, the prismatic effect itself can be obtained by entering the collimator off-axis on one side 102 and appropriately angulating the second element of the collimator 104.

At the other end of the AOM 66, a similar prism and beam expander will realign the different wavelength laserbeams and provide the required beam diameter. In view of what will follow, it is not unusual to obtain a fairly large beam diameter, larger than 1 mm, suitable for truncation at some further point in the illuminating pathway.

It is also understood that the prisms are not necessary if only one wavelength is used for which a short rise time is desired. Rise-times in the order of 30 ns, which are definitely subpixel, are not difficult to obtain and compare favorably with the currently used rise-times of about 200 ns (beyond two pixels of duration)

As further explained, if both IR and visible wavelengths are equipped with appropriate AOMs, then a number of possibilities exist with regard to multiplexing the SLO with MP and SD-OCT, avoiding the need of multiple synchronized detector pathways. When passing different wavelengths through one AOM it should also be noted that the RF power efficiency when modulating is related to wavelength, even at the correct Bragg angle for each wavelength. The manuals and specification sheets of IntraAction Inc. AOM models E801D6 80 MHz driver and ATM-80A1 are a reference. For refractive index values of different Schott type glasses such as BK-7, and the specifications of dispersing prisms we refer again to the tabular data of Melle-Griot catalogue, copyright 2002.

II. Enhanced Aperture for Separating Light Pathways Inside the SLO

Every opthalmoscope since its conception needs to separate at one point the illuminating pathway from the pathway that is followed by the returned light. Obviously because the illuminating source and the observer's eye (or detector) cannot be in the same place, but perhaps more pertinent to understand, the need to avoid strong reflexes from mostly the anterior surface of the cornea. This can be accomplished in two ways. A central stop or aperture 24 is used to separate both pathways. Conveniently the aperture's size and location are such that all of the spurious reflexes are transmitted or stopped by the same stop or aperture (essentially returning to the light source itself). This mechanism is found traditionally in opthalmoscopes and fundus cameras of all sorts. Confocal (scanning) microscopes use the fact that if the detector is confocal with the object, reflexes coming from other layers would arrive at this detector much diluted and would therefore not contribute significantly to an undesirable contrast reduction. Although this principle, thus solely using a beamsplitter, alone could be used in a confocal SLO to accomplish this, the relaxed confocal design of the SLO—which means that the confocal aperture 16, 18 is at least four times larger in diameter than the illuminating laser spot on the retina—would render this mechanism inadequate. Only a tightly confocal instrument could therefore use a beamsplitter to this effect.

Figure 8:
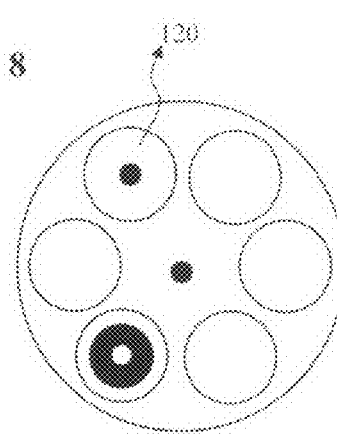
FIG. 8 shows a filter wheel combining several options with regard to truncation of the laser beams and reflection characteristics of light that is returned from the eye.

As a result, the separating aperture 24 in the relaxed confocal SLO is wholly transparent. Under the current invention we propose to provide a series of apertures 120, e.g. placed on a larger rotating wheel to be able to select one at will (FIG. 8), with the following characteristics:

(1) The (Gaussian) illuminating laser beams in the SLO can be truncated 116 at this point to different diameters and even an elliptical shape. On a side, such elliptical beam shaping can also occur just prior to the aperture with the help of cylindrical lenses or more appropriately anamorphic prisms 152. Truncation of the Gaussian beams 132 allows a diffraction limited spot to focus onto the retina but instead of the Gaussian beam formulas, the classic diffraction limited aperture formula will be applicable. With other words, if the initial beam diameter is 3 mm Gaussian 124, it can be stopped down by the aperture 116 to 1 mm, be far more even in illumination and result in a substantially smaller spot on the retina than if a 1 mm Gaussian beam 128 diameter was used.

Figure 7:
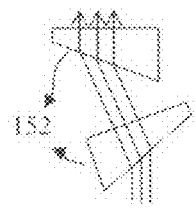
FIG. 7 illustrates an alternative embodiment separating several functions such as beam shaping (FIG. 7 a), truncation (FIG. 7 b) and multizone coatings (FIG. 7 c) of the separating aperture.
Figure 7:
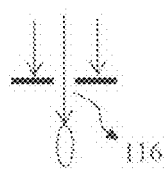
Figure 7:
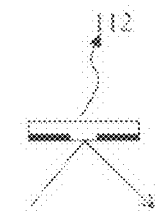

(2) The aperture 116 itself can consist of clear glass that is coated in such way that different wavelengths, e.g. imaging vs. psychophysics wavelength can have a different beam diameter, but still be collimated beyond the aperture (FIG. 7b). To summarize this point, a variable aperture can control the diameter (and shape) of the focused spot on the retina. Thereby the need for complex collimator-telescopes is avoided in the illuminating pathway.

(3) The aperture 24 can be coated on the side facing the returning light 112 to specifically return to the detectors valuable diagnostic light coming from the retina that would otherwise pass through the opening. This is particularly the case for laser light from external light sources attached to the SLO in a manner already described. E.g. to measure the directionality of the photoreceptors, the waveguided light inside the photoreceptors will be reflected back along the same path (and not be multiply scattered). To collect this light efficiently, such aperture is highly advantageous. It is possible to conceive of situations where the illuminating laser light from the SLO itself needs to be retrieved. What about the spurious reflections in this case? It has been clarified before that the reflexes occur practically exclusively when the illuminating scanning laser reaches the apex of the cornea (otherwise it is reflected off to the side), or in an special single situation where at all angles the illuminating laser is more or less perpendicular to the corneal surface. We simply avoid this position and to eliminate the corneal reflex, we can acousto-optically modulate the sources whether external or internal to be off for this position.

The confocal detecting apertures 16, 18 also come in different diameters, with a central stop, and coatings. It is possible to create asymetric apertures to emulate indirect lighting from one side.

With regard to the illustrations we refer to the Melles-Griot catalogue optics information on truncation of Gaussian beams, copyright 2002.

III. Enhanced Electro-Optical Control of the Galvanometer-Polygon Scanning Elements within the SLO Early co-pupillary SLO designs by Pomerantzeff and Webb used two mirror-galvanometers 22 in tandem to obtain the desired scanning laser raster. Remarkable at that time was the flexibility of the laser raster dimensions by simply varying the amplitude and frequencies of these galvanometers. Later confocal SLO models adhered closely to the universal NTSC or PAL television standards for generating the raster. Also, the speedier polygon 20 was introduced for fast horizontal scanning. Typically, the polygon would run at about 40,000 RPM and would have either 24 or 25 facets to create the horizontal raster lines. The vertical scanning is typically 50 or 60 Hz, interlaced. Interlacing has a long history dating back to the origin of TV. It exists to conserve bandwidth and to cope with psychophysical flicker that would otherwise be visible to the observer. Zooming in such an SLO is typically accomplished with the help of a Campini type of telescope-invertor 42. It conveniently changes the horizontal angle of deflection between two values, and also at the same time adjust the beam diameter of the illuminating lasers. Such constellation is seen in the prior art FIGS. 1 and 2.

Figure 9:
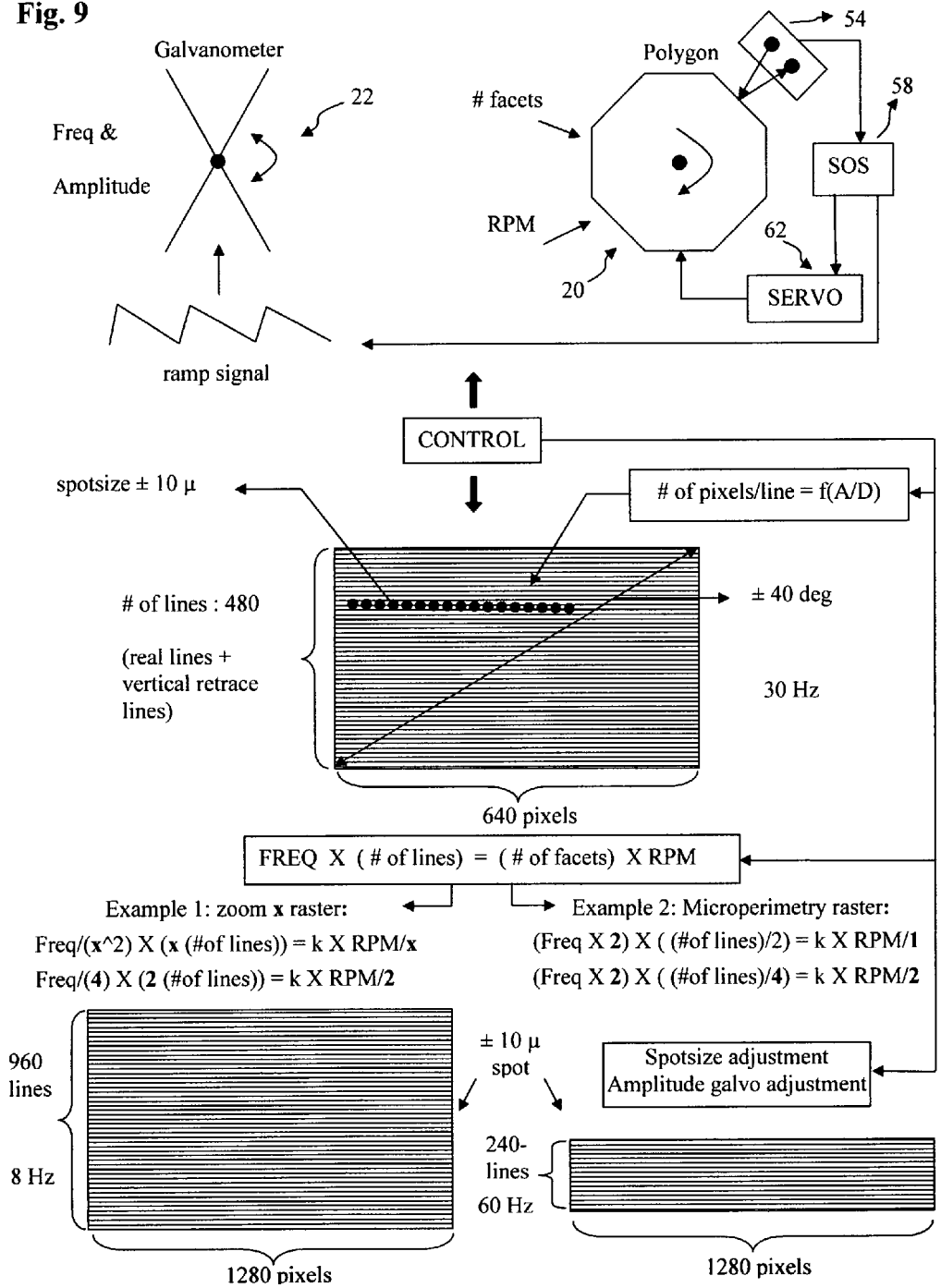
FIG. 9 demonstrates the flexibility in controlling the scanning elements polygon and galvanometer. Zoom effects or rasters that are particularly suited for MP and OCT are illustrated.
Figure 10:
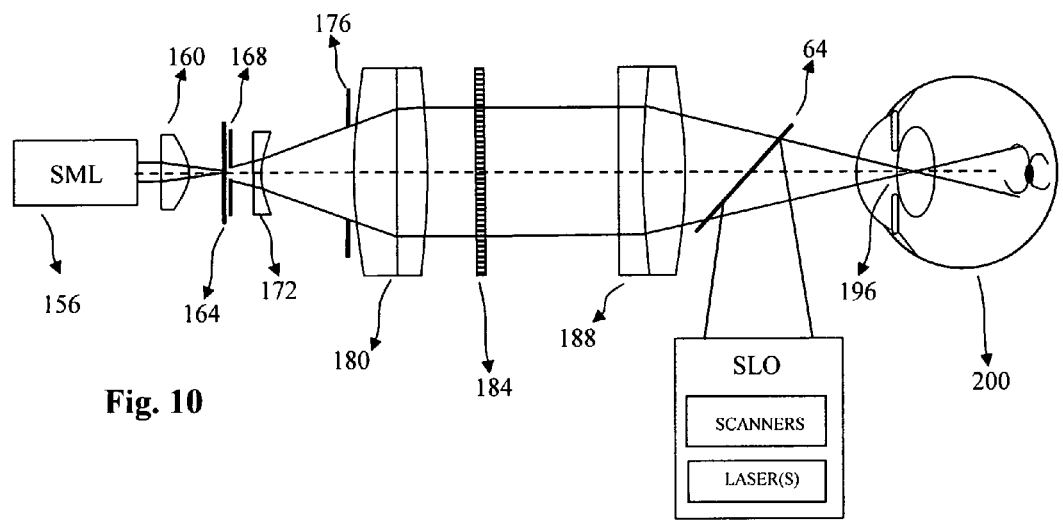
FIG. 10 illustrates the use of a LC-SLM as modifying element in a Maxwellian view projection system. Additional lens modules can be incorporated.
Figure 11:
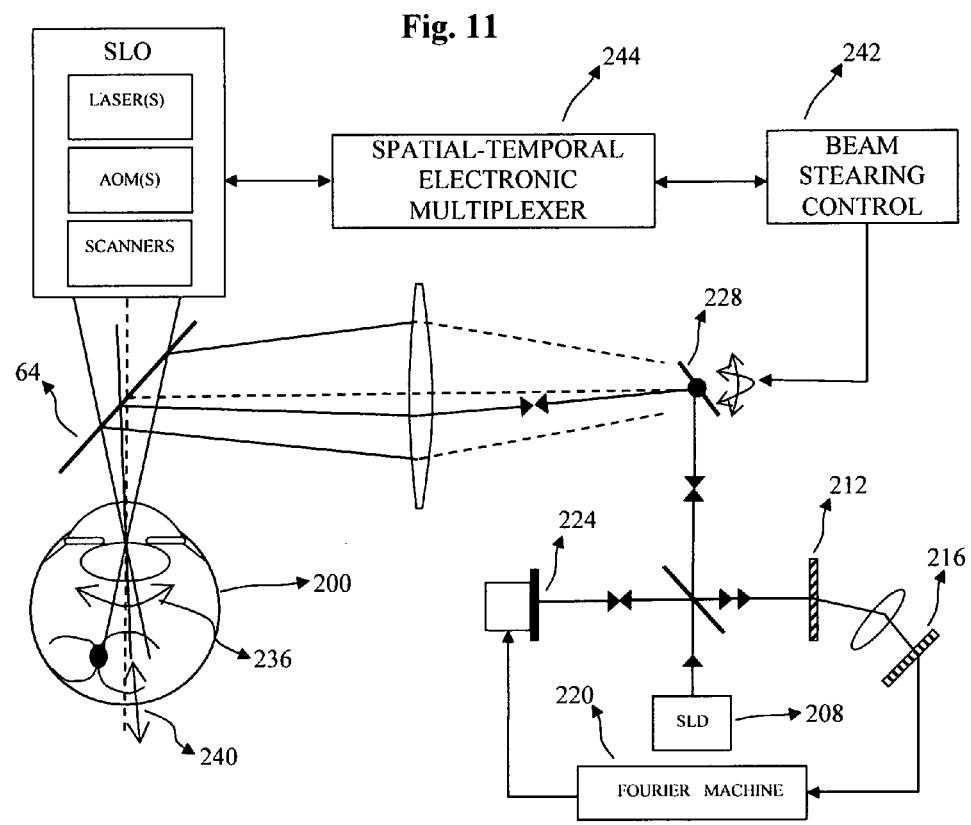
FIG. 11 shows a combination of a prior art SLO (Van de Velde) and prior art SD-OCT (Fercher) to obtain a functional SLO-SD-OCT combination. Multiplexing (spatial-temporal) is provided, as well as coordination with the beam steering control.

There is a tendency to digitally create and control both video in and out for the SLO, and one result is that video standards have become more flexible with regard to refresh rates and pixel dimensions. The SLO can take advantage of this by electronically adjusting the polygon and galvanometer characteristics (FIG. 9), rather than by inserting additional optical elements. This renders the instrument more compact and economical. As will be explained, the previously mentioned capability of beam truncation 116 is important in this respect. It is important to understand that the laser raster characteristics or requirements are different for imaging or psychophysical purposes. This will be explained below.

One formula is basic to our discussion: it describes the relation between the number of image lines (raster lines), including any number of "virtual" lines drawn during the vertical retrace, the number of facets on the polygon 20, the polygon speed and the refresh rate of the raster that is determined by the galvanometer 22. The formula is thus:

$$(\text{Refresh Frequency}) \times (\text{\# of lines}) = (\text{\# of facets}) \times (\text{RPM of polygon}).$$

This formula is applicable to both interlaced or non-interlaced schemes. Note that the angular amplitude of the galvanometer 22 and the actual beam diameter of the flying spot on the retina do not appear in this formula. Those last two parameters are to be independently controlled.

By varying the above mentioned parameters the following results can be obtained:

(1) in a generic laser raster, using e.g. the NTSC standard, the interlaced video is 30 Hz for 525 "TV" lines. The A/D converter, of which the speed determines the number of pixels per line for given (fixed) formula parameters, transforms the image into a 640 by 480 "square" pixel format. The number of facets is 25. Optimally the number of facets is a real number fraction of the total number of lines to ensure that the same facet always draws the same line in the raster. Otherwise, small discrepancies (wobble) in facet orientation may cause noise or ripple in the image. Current polygons suffer much less from this problem. The resultant RPM for this embodiment is therefore 30×525 divided by 25, i.e. 630 rounds per second or usually expressed as 37,800 RPM. This speed is kept constant through a PLL crystal driven servo mechanism. A trigger is derived as a master clock signal from each turning facet in a matter described before. Because we control extremely well the timing, the precise temporal resolution of the image has been proposed by us before to obtain an excellent spatial resolution for wavefront analysis purposes.

(2) One raster modification is reminiscent of the original zoom mechanism that was implemented by Pomerantzeff et Al. in their first co-pupillary SLOs. If the same A/D conversion is used but the polygon slows down by a factor of 2 (or more generally x fold), the frequency of the galvanometer is reduced by 4 (or generally x^2), thus, in combination, the number of horizontal lines that are drawn will double (or increase x fold). The formula holds as the number of facets obviously remains the same. For imaging purposes, the spot diameter on the retina will not change. Although this may seem rather strange, it should be observed that the light being collected is more determined from the size of the confocal aperture than from the initial impact zone on the retina. This means that basically the same image area on the retina will be visualized, for example a 40 degree diagonal FOV, regardless of zoom, but the magnification factor changes, i.e. the number of horizontal and vertical pixels. The price that is paid for a lower resolution is "subsampling" of the same area on the retina, the bonus we get is increased refresh rate. This increase in refresh rate (or decrease) has some implications in the presence of eye movements and has a very important impact on psychophysical applications because of the human eye's sensitivity to flicker under certain conditions. Three types of fixational eye movements exist that merit our attention: a very fast 60 Hz, small amplitude oscillation that is generally below the resolution of a regular SLO (not adaptive optics SLO). A second movement is a slow drifting of typically 1 degree per second. In general this will only cause a slight distortion of the consecutive images even at low refresh rates. For the purpose of fiducial landmark tracking, these movements will not affect close TV lines but might lines that are spaced at the edges of the screen. A third type of eye movement are the "corrective" micro-saccades" or flicks. They are a rapid restoration of the line of sight onto the object of fixation. Such flicks will either cause a clearly visible abrupt shift in the image, visible as a break or discontinuation of the vessel pattern upon freezing the image or they will cause the same fiducial landmarks to be appreciably separated from each other in consecutive images. During active tracking using e.g. two-dimensional normalized gray-scale correlation these flicks can be distinguished from the slower drifting based on aforementioned characteristics. Because of this and because of the typical distortion of the laser raster, fiducial landmarks for tracking should be chosen as close as possible to the area of interest to be tracked.

(3) Another problem occurs when we not only image the retina, but perform psychophysics in a manner that has been described before using relatively low intensity visible laser wavelengths and acousto-optic modulation. From psychophysics we know that only the use of a low visible background intensity with fairly small stimulus sizes will have a chance to be not affected by a 30 Hz flicker sensation; and those backgrounds will typically be 100 trolands or less. SLOs that use interlaced video at 60 Hz can use a large bright background with dark stimuli e.g. to measure visual acuity. How can we solve this problem if the polygon speed cannot be further increased or the galvanometer has reached its limitations with regard to refresh frequency given a certain mirror load and angular amplitude? This situation can be addressed as thus: in the basic formula we double the frequency of update, we divide the number of lines by 4 and reduce the RPM of the polygon by a factor of 2. Therefore horizontally we get indeed a doubling of the number of pixels. At the same time the angular amplitude of the galvanometer is cut in half as well. Most galvanometers can indeed trade amplitude for refresh rate to some extent given a certain mirror load. In summary, we obtain a 60 Hz non-interlaced display of 120 lines over the full available width of the raster at increased (double) resolution: this is an advantageous situation for text display and acuity testing.

(4) Typically, the spot size on the retina of the visible laser should be appropriate to cause the pixels to fill up smoothly with no overlap or any appreciable "empty" space between the raster lines. As mentioned before, this smaller size can be used if less magnification is used for imaging purposes, but would be problematic in the case of psychophysics. If that situation arises, the spot size can be adjusted through aperture and beamshaping control of the laser that is responsible for the visible light (aforementioned adjustable beam truncation 116).

(5) Adjustment of the angular vertical amplitude of the laser raster with the galvanometer 22 is useful in other situations: e.g. to calibrate square pixels; and if the lines are made to overlap, a higher resolution can be obtained when confocaly detecting the position of the laser spots projected by the previously mentioned external wavefront measurement module.

IV. Interfacing with External Light Sources for Purpose of MP, Using Spatial Light Modulation Some embodiments have been described in the references. For example, Selective PDT or TTT laser treatment to the retina (U.S. Pat. No. 6,186,628). PDT or TTT requires a fairly large amount of power to be delivered to the retina, hence the use of a higher powered multimode laser and a simple mode scrambling device. The spatial pattern that is desired is most often stationary and requires only some adjustment in positioning if the retina were to move. The laser light is delivered in Maxwellian view mode 196, using two possibilities of combination 64.

If a low power laser source 156 is used to generate MP graphics, the laser could first be focused 160 to a very small spot (10 micron) onto a thin diffuser 164. On the other side of the diffuser a pinhole 168 (50 micron) is attached from which the light will fan out, its coherence being broken. Divergence can be controlled if necessary with a negative lens 172. The N.A. can be fixed with a subsequent large aperture 176 (about 10 mm) and collimation 180 will prepare the bundle of light to hit the LC-SLM 184, a spatial light modulator situated in a retinal conjugate plane. Several adjacent pixels under CPU control would let an approximately 1 mm entrance diameter beam travel towards the pupil and retina in Maxwellian view 196.

Using the Maxwellian view projection of the TTT method and the LC-SLM described above, it is thus possible to project microperimetric stimuli onto to the retina. Additional modules comprising lenses, can be inserted in the optical pathway to take care of magnification or focus issues. These extra modules have been omitted from the drawings. The single mode laser 156 can be replaced with a conventional light source. For further reference we include by reference a paper presented at the International Conference on Lasers '96, Society of Optical and Quantum Electronics, 2-6 Dec. 1996, entitled "Applications of programmable spatial light modulators", and selected references, by author Michael K. Giles.

V. Interfacing with Fast Scanning External Light Sources for the Purpose of Multiplexing with SD-OCT The electro-optical characteristics of the relaxed confocal scanning laser opthalmoscope can be used to great benefit when combining this instrument with external laser sources, in particular scanning laser sources. Several examples of increasing complexity have been outlined in the incorporated patents by reference. We would like to give an overview and describe an additional possibility, SD-OCT.

For therapeutic purposes there has been an increasing interest in targeting selectively the retinal pigment epithelium—although we could argue for some reasons that preferably the photoreceptor outer segments should be disabled in a certain pattern, or "holes" created within an obstructive and thickened Bruch's membrane. The technique has been referred to as microphotocoagulation. In brief, scanning is performed with the help of a two dimensional or one-dimensional acousto-optic deflector. The details have been outlined in U.S. Pat. No. 6,789,900.

There is an important diagnostic application when scanning external light sources for the integration of spectral domain optical coherence tomography (SD-OCT) into the SLO, based on some general principles outlined before and taking into account some particular observations with regard to the use of SD-OCT itself.

Figure 5:
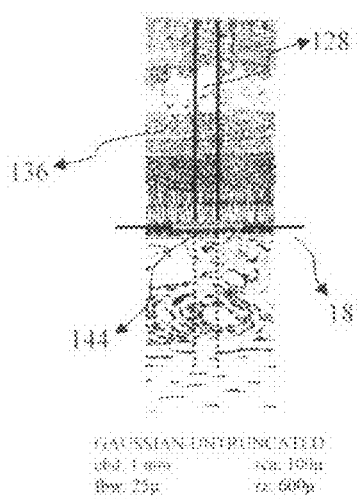
Figure 5:
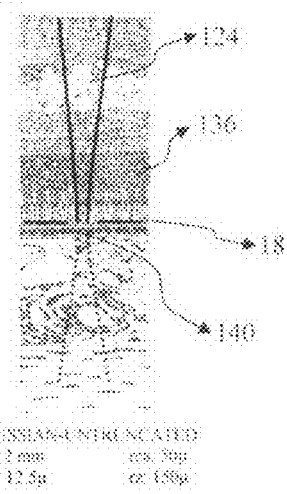
Figure 6:
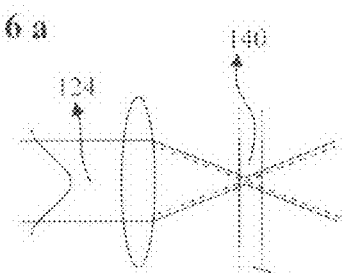
FIG. 6 demonstrates the difference between pure Gaussian optics (FIGS. 6 a and b) and truncation (FIG. 6 c, classic diffractive pattern) in focusing within the human eye (schematic).
Figure 6:
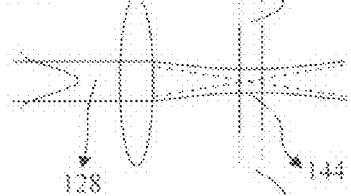
Figure 6:
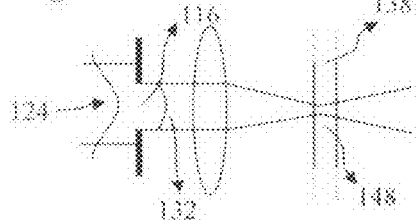

In brief, SD-OCT was conceived by Fercher in 1995 as an alternative to the classic time domain OCT. This time domain OCT requires a lay-out that is similar to a Michelson interferometer to record reflections within the retina (Thus exploring the retina in depth or z-direction 240; the SLO typical explores the x-y plane 236 and sort of integrates the information from the z direction). The time domain OCT requires a reference arm that rapidly scans back and forth. This is fairly time consuming. Using broadband light sources, this interference method can obtain a resolution in the z-direction of as little as 5 micron. This compares very favorably with the limited z-resolution of a confocal SLO which is at best about 150 micron (FIG. 5b). Thus both diagnostic techniques are very complimentary and their combination would give rise to an instrument in which the ophthalmologist has an immediate overview of the retina and where he would be able to obtain a section of histological quality 136, 140 (much like a slitlamp would do) between any two points of interest.

Up to now such combinations exist, combining a variation of a classic fundus camera with time domain OCT. However several disadvantages exist: the time domain is slow, about 400 samples can be taken per second, several thousand are needed to collect a reasonable amount of information. In this time interval, eye movements occur and also, the fundus visualization is either non-confocal IR which does not permit viewing details on the retina, or it is a color reference picture on which it is difficult to outline precisely where the OCT samples have been taken.

Some of these problems have been resolved by constructing an SLO-OCT combination (Podoleanu) that uses the x-y scanning lasers to obtain the interference data as it scans along a raster pattern on the retina (C-plane scanning). This however does not resolve some of the issues regarding speed, S/N ratio and immunity against eye movements, since the technique is still essentially within the time domain.

Our SLO-OCT combination is based on the spectral domain method 212, 216 and exploits the unique capabilities to combine scanning laser sources as described in referenced patents. Only recently has SD-OCT become mainstream (in combination with a classic slitlamp or fundus camera) because of the intense calculations (Fourier transforms) that have to be performed. Current computational devices 220 are up to this task and it is not unusual to be able to derive 40,000 samples per second. It is precisely this high speed acquisition of information that makes integration within the SLO possible. Besides the general issues that have been addressed in previous patents and for which the solutions are here applicable by comparison, two special considerations have to be made:

(1) SD-OCT using a broad-band light source 208, e.g. in the near-infrared region with subsequent spectral analysis of the returned light that was subject to interference. The SLO typically and for ease of implementation also uses near-infrared light 10. We want to preserve our near real-time capability of observing the retina (and eye movements) and have a near real-time histological sectioning 136, 140 as well: the answer to this problem lies in multiplexing of the two information channels (SLO and OCT). For this purpose, the CPU unit 242, 244 does know the coordinates and timing of the OCT sampling. This computer also controls the modulation of the IR laser source (and any visible laser sources) within the SLO for x-y scanning. Such modulation whether TTL based or AOM based, is flexible enough to permit both the SLO and OCT to gather information with minimal delay or near real-time, without interfering with each other.

(2) Along the same lines it can be understood that active two dimensional normalized gray-scale correlation tracking of fundus landmarks in the vicinity of the histological section is possible at video-rates.

The two systems (SD-OCT and relaxed confocal SLO) can be combined optically 64 using similar constructions as described in previous patents. Ideally, the scanning of the OCT component happens to originate from a pivot point 228 and through the similar pivot point of the SLO scanning lasers. The module can be completely external, or it can still make use of the main reflecting mirror inside the SLO. In the later case, the pivoting mechanism is smaller and consist of a mirror that is allowed to move in x-y directions on top of a ball bearing. Focusing however requires at least one more lens element. At this point it is useful to remind that fast IR modulation (TTL or AOM based) can have an additional application in video blanking for microperimetry purposes: when measuring absolute thresholds on the retina; even "invisible" IR light of 800 nm still retains the capability of stimulation the retina: the IR laser could then be turned of in the neighborhood of the stimulus. Also multiplexing in the case of combined ICG and fluorescein angiography, and multiplexing in general when only one detector pathway instead of two are available, are important applications of fast IR modulation.

As a last remark we point to the development of polarization sensitive OCT techniques: these would have the capability of analyzing the state of polarization, hence birefringence of the nerve fiber layer in the retina based on an absolute high resolution space interval (typically 3 micron). This cannot be realized with the current polarization sensitive SLOs that suffer from the interference of corneal birefringence, and measure the total birefringence of the nerve fiber layer. Such technique cannot readily distinguish between true nerve fiber layer thinning and molecular changes (microtubules) within the nerve fiber axons that e.g. limit axonal transport in the early stages of neuro-degenerative diseases such as glaucoma and Alzheimer's.

For further information on SD-OCT we include by reference the following U.S. Pat. No. 6,377,349 by Adolf Fercher, and also refer to the following publications: (1) Measurement of intraocular distances by backscattering spectral interferometry, in: Optics Communications, by A. Fercher et Al, 1995; (2) Optical Coherence Tomography in: Journal of biomedical optics, vol 1(2) pp 157-173 1995 by A. Fercher; (3) Optical coherence with spectral radar by M. Bail et Al., in: Photon Propagation in Tissues II, Proc. SPIE vol 2925, page 298-303, 1996.

SUMMARY

Embodiments of the relaxed confocal scanning laser opthalmoscope have been disclosed that relate to:

(1) an improved modulation of visible and IR lasers, with regard to optical rise-time and combination of wavelengths;

(2) an aperture controlled truncation of the illuminating laser beams and coating of such aperture to preferentially reflect on-axis returned light to the detectors of the SLO;
(3) variations on the basic scanning formula "Freq× lines=number of facets×RPM," whereby complications of a low refresh rate and resolution are avoided for certain psychophysical tests;
(4) alternative use of a liquid crystal spatial light modulator for microperimetric purposes;
(5) a combination of the SLO with fast scanning external light sources, in particular the light sources that are employed in spectral domain optical coherence reflectometry or tomography.

Although the descriptions above contain many specifications, these should not be construed as limiting the scope of the invention but as merely providing an illustration of the presently preferred embodiments. Other embodiments including additions, subtractions, deletions, or modifications will be obvious to those skilled in the art and are within the scope of the following claims. The scope of the disclosure should be determined by the appended claims and their legal equivalents, rather than by the examples given.

I claim:

1. A scanning laser opthalmoscope apparatus for projecting a two-dimensional pattern of light of variable intensity and resolution onto the retina of an eye comprising the elements of:
    a laser source means, emitting a beam of light with a wavelength in the visible range and having a beam diameter that is large enough and depth of focus that is large enough to transmit and focus said beam within said apparatus over a distance;
    a first focusing means for reducing substantially the beam diameter and reducing accordingly the depth of focus of said beam of light;
    an acousto-optic modulating means comprising crystal optics with an optical axis and of certain small dimension wherein sound waves propagate with a certain velocity, and electronic driver means emitting a modulated radio signal of certain frequency for creating said sound waves, said first focusing means and said crystal optics placed at a distance from each other and in such manner that said beam of light will focus optimally inside said crystal optics at an angle relative to said optical axis, said angle determined by said wavelength, said radio frequency and said sound velocity, and said radio frequency high enough to cause said sound waves to diffract said beam of light of reduced beam diameter efficiently in a minimum amount of time into a first order modulated beam of light of reduced beam diameter;
    a beam expanding means for enlarging the beam diameter of said first order diffracted and modulated beam of light leaving said crystal optics at said angle relative to said optical axis to enable again further focusing within said apparatus over a distance;
    a scanning means including horizontal polygon scanning means, vertical scanning means and second focusing means, to direct and focus said modulated and first order diffracted beam of light onto said retina of an eye, whereby a very high modulation bandwidth is obtained for the projection of said two-dimensional pattern of light relative to the bandwidth of imaging for said apparatus.

2. A scanning laser opthalmoscope apparatus for projecting a two-dimensional pattern of light of variable intensity and resolution onto the retina of an eye according to claim 1, further comprising the elements of:
    a second laser source means, emitting a second beam of light with a second wavelength in the visible range and having second angle for optimal diffraction within said optical crystal;
    a dispersive optical element for causing a certain angular divergence between said beam of light and said second beam of light;
    said dispersive optical element and said first focusing means positioned relative to each other and relative to said crystal optics so that the angular divergence of said beam of light and said second beam of light is inverted before said beam of light and second beam of light enter said crystal optics.

3. A scanning laser opthalmoscope apparatus according to claim 2 wherein said dispersive optical element is a convex lens element.

4. A scanning laser opthalmoscope apparatus for projecting and registering a two-dimensional pattern of light of variable intensity and resolution onto the retina of an eye comprising the elements of:
    infra-red laser light source means emitting a laser beam of wavelength in the infra-red spectrum;
    scanning means comprising a first scanning element for horizontal deflection of said laser beam, and second scanning element for vertical deflection of said laser beam, both deflections causing a scanning of said laser beam through a pivotal region of small cross-sectional area according to a pattern of parallel lines onto said retina of an eye by said laser beam;
    beam shaping means for focusing said laser beam onto a desired confocal plane within said retina of an eye;
    confocal detecting means for collecting reflection of light over time from said retina of an eye, using said scanning means in reverse order, and outputting an electrical signal varying according to the strength of said reflection of light;
    display means for showing, storing and updating over time said electrical signal as a two-dimensional image on a monitor;
    and further comprising the elements of:
    a light source means emitting light of at least one wavelength in the visible spectrum;
    a first optical focusing means for concentrating said light of said light source means;
    aperture means positioned to receive a maximum intensity of said light from said light source means, and said aperture means having sufficiently small diameter to direct said light through said pivotal region of small cross-sectional area;
    second optical focusing element for collimating said light of said light source means after passing of said light through first focusing means and aperture means;
    modulating means for spatially modulating light along two dimensions, comprising a plurality of individually addressable pixel elements of which the transparency is according to a graphical representation;
    third optical focusing means to redirect said light of said light source means through said pivotal region of small cross-sectional area and to position said modulating means at said desired confocal plane within said retina of an eye; and
    beam splitter means positioned to direct said light of said light source and said laser beam through said pivotal region of small cross-sectional area and to direct said reflection of light from said retina to said confocal detection means, whereby said graphical representation is localized on said two-dimensional image of said retina even in the presence of movements of said eye.

5. A scanning laser opthalmoscope apparatus for projecting and registering a two-dimensional pattern of light of variable intensity and resolution onto the retina of an eye according to claim 4 wherein said light source means is a coherent laser light source emitting in the visible spectrum, and further comprising a coherence breaking optical element means whereby the psychophysical observation of speckle formation onto said retina of an eye is removed.

6. A scanning opthalmoscope apparatus for obtaining three-dimensional reflection characteristics of the retina of an eye, comprising:
   infra-red laser light source means emitting a laser beam of a wavelength in the infra-red spectrum;
   first scanning means comprising a first scanning element for horizontal deflection of said laser beam, and second scanning element for vertical deflection of said laser beam, both deflections causing a progressive scanning of said laser beam through a pivotal region of small cross-sectional area onto said retina of an eye according to a pattern of parallel lines;
   beam shaping means for focusing said laser beam onto a desired confocal plane within said retina of an eye;
   confocal detecting means for collecting reflection of light over a specified interval of time from said retina of an eye, using said scanning means in reverse order, and outputting an electrical signal varying according to the strength of said backscattering of light;
   display means for showing, storing, and updating over said interval of time said electrical signal as a two-dimensional image on a monitor;
   and further comprising the elements of:
   a light source emitting a first beam of light comprising a plurality of wavelengths;
   first beam splitting means for dividing said beam of light into a second beam of light and third beam of light;
   a reference mirror for returning said second beam of light to said first beam splitter means;
   second scanning means including a plurality of moving mirrors and two-dimensional beam position controlling means for scanning according to a second pattern of parallel lines over a second interval of time;
   second beam splitting means positioned to direct said laser beam and said second beam of light through said pivotal region of small cross-sectional area;
   spectrally resolved intensity detector means for measuring the power spectrum of the interference of returned said second beam of light with reflected light of said first beam of light from said retina;
   Fourier machine means for analyzing the output of said spectral intensity detection means to represent reflection characteristics of said retina of an eye for a dimension that is perpendicular to said two-dimensional image of said eye, along said second pattern of parallel lines; and
   multiplexing means to synchronize scanning along said first pattern of parallel lines with scanning along second pattern of parallel lines and thereby allowing a three-dimensional representation of reflection characteristics from said retina of an eye even in the presence of movements of said eye.

* * * * *